United States Patent
Garland et al.

(10) Patent No.: US 11,390,626 B2
(45) Date of Patent: Jul. 19, 2022

(54) PYRAZOLOPYRIMIDINE MODULATORS OF RAS GTPASE

(71) Applicant: Tosk, Inc., Mountain View, CA (US)

(72) Inventors: William A. Garland, Mountain View, CA (US); Solomon B. Ungashe, Mountain View, CA (US); Stephen D. Yanofsky, Mountain View, CA (US); Philip Liaw, Mountain View, CA (US); Annie L. Lennek, Mountain View, CA (US)

(73) Assignee: Tosk, Inc., Mountain View, CA (US)

( * ) Notice: Subject to any disclaimer, the term of this patent is extended or adjusted under 35 U.S.C. 154(b) by 120 days.

(21) Appl. No.: 16/774,381

(22) Filed: Jan. 28, 2020

(65) Prior Publication Data

US 2020/0239479 A1    Jul. 30, 2020

Related U.S. Application Data

(60) Provisional application No. 62/798,319, filed on Jan. 29, 2019.

(51) Int. Cl.
    *C07D 487/04*      (2006.01)
    *A61P 35/00*      (2006.01)

(52) U.S. Cl.
    CPC ............ *C07D 487/04* (2013.01); *A61P 35/00* (2018.01)

(58) Field of Classification Search
    CPC .............................. A61P 35/00; C07D 487/04
    See application file for complete search history.

(56) References Cited

U.S. PATENT DOCUMENTS

| | | | |
|---|---|---|---|
| 2018/0086752 A1 | 3/2018 | Rabizadeh et al. | |
| 2018/0155348 A1* | 6/2018 | Li | C07D 491/04 |
| 2019/0022074 A1* | 1/2019 | Hadari | C12N 15/1037 |
| 2019/0134056 A1* | 5/2019 | Tolias | A61K 31/454 |

FOREIGN PATENT DOCUMENTS

| | | | |
|---|---|---|---|
| KR | 10-2011-0114663 A | 10/2011 | |
| WO | WO0202563 A2 | 1/2002 | |
| WO | WO2005012256 A1 | 2/2005 | |
| WO | WO2017023133 A2 | 2/2017 | |
| WO | WO 2020/127200 * | 6/2020 | ........... C07D 401/14 |
| WO | WO 2020/132071 * | 6/2020 | ........... C07D 401/04 |
| WO | WO2020180768 A1 | 9/2020 | |
| WO | WO2020180770 A1 | 9/2020 | |

OTHER PUBLICATIONS

Kaswan et al., Synthesis of 5,7-diarylpyrazolo [1,5-a] pyrimidines via KOH mediated tandem reaction of 1H-pyrazol-3-amines and chalcones, Tetrahedron Letters, 2015, vol. 56, No. 3, pp. 549-553.
Compton et al., Pyrazolo [1,5-a] pyrimidines: estrogen receptor ligands possessing estrogen receptor β antagonist activity, J. Med. Chem., 2004, vol. 47, No. 24, pp. 5872-5893.
Ouiroga et al., Regioselective formylation of pyrazolo [3,4-b] pyridine and pyrazolo [1,5-a] pyrimidine systems using Vilsmeier-Haack conditions, Tetrahedron Letters, 2008, vol. 49, No. 17, pp. 2689-2691.
McCarthy et al., Discovery of High-Affinity Noncovalent Allosteric KRAS Inhibitors That Disrupt Effector Binding, ACS Omega, 2019, vol. 4, p. 2921-2930.
Chemical Abstract compounds, STN express RN 1269064-16-5 (Entered STN: Mar. 21, 2011).
Chemical Abstract compounds, STN express RN 2109536-59-4 (Entered STN: Aug. 7, 2017).
Chemical Abstract compounds, STN express RN 1360253-07-1 (Entered STN: Mar. 7, 2012).

* cited by examiner

*Primary Examiner* — Erich A Leeser
(74) *Attorney, Agent, or Firm* — Peter W. Schroen; Bret E. Field; Bozicevic, Field & Francis LLP

(57) ABSTRACT

Pyrazolopyrimidine RAS modulating compounds and methods of using the same are provided. The pyrazolopyrimidine compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

16 Claims, 3 Drawing Sheets

Normal Flies

Flies Expressing G12V in Their Wings

Flies Treated with Trametanib

PYRAZOLOPYRIMIDINE MODULATORS OF RAS GTPASE

CROSS-REFERENCE TO RELATED APPLICATION

Pursuant to 35 U.S.C. § 119 (e), this application claims priority to the filing date of U.S. Provisional Patent Application Ser. No. 62/798,319 filed Jan. 29, 2019; the disclosure of which application is herein incorporated by reference.

GOVERNMENT RIGHTS

This invention was made with government support under grant No. 1R43CA189549-01, awarded by the Department of Health and Human Services. The government has certain rights in the invention.

INTRODUCTION

The RAS family of proteins represents a group of 189 amino acid (21 kDa molecular mass), closely related, monomeric, globular GTPases which associate with the plasma membrane and bind either guanosine diphosphate (GDP) or guanosine triphosphate (GTP). The proteins act as molecular switches in signal transduction in cells. When bound to GDP, RAS is in its off (resting) position and is inactive. When activated by its cell surface growth factor EGF, RAS exchanges bound GDP for GTP. With GTP bound, RAS is "switched on" and can interact with, and activate, other proteins including its "downstream targets," such as the pro-growth Ras-Raf-MEK-ERK pathway. The RAS protein itself has a very low intrinsic ability to turn itself off by hydrolyzing GTP back to GDP. Switching RAS off requires extrinsic proteins termed GTPase-activating proteins (GAPS) that interact with RAS and greatly accelerate the conversion of GTP to GDP. Any mutation in RAS which affects its ability to interact with a GAP or to convert GTP back to GDP can result in a prolonged activation of the protein and consequently provide a prolonged signal to cells to proliferate. Because these signals result in cell growth and division, overactive RAS signaling can lead to cancer. Conversely, compounds that bind the inactive GDP-bound RAS and inhibit the exchange of GDP for GTP inhibit RAS activity by preventing its association with, and activation of, its downstream targets. Compounds that inhibit the association of activated GTP-bound RAS with its downstream targets such as the RAF family of proteins also inhibit RAS-induced promotion of cell growth and proliferation and are of interest as potential anti-cancer drugs.

Mutations in any one of the three main isoforms of RAS (hRAS, nRAS, or kRAS) genes are among the most common events in human tumorigenesis. About 30% of all human tumors are found to carry some mutation in RAS. Most of these mutations 86% are in kRAS. By comparison, the rates of oncogenic mutation occurring in the nRAS and hRAS family members are much lower (11% and 3% respectively). The most common kRAS mutations are at residue G12 and G13 in the P-loop and at residue Q61. kRAS is mutated in at least 61% of pancreatic cancers, 43% of colon cancers, 21% of endometrial cancers, 26% of lung adenocarcinomas, eg, NSCLC, 3% of skin cancers, 4% of acute myeloid leukemia (AML) liquid tumors and in 1% or so of multiple myeloma cancers.

Based on the common occurrence of mutated kRAS protein in tumors and pro-growth signaling activity of the mutated kRAS protein, an effective kRAS modulating compound could play an important role in treating cancer.

*Drosophila melanogaster* flies can be utilized as media for initial screening for RAS modulating compounds. Task has created a fruit fly with human kRAS G12V expressed in its wing. The mutant kRAS expressed in the fly wing appears functional, even though it operates in the presence of the other physiological systems present in the fly. The fly phenotype in the mutant fly is a crimped wing which can be reversed to a great extent if the fly is fed food enriched an effective kRAS inhibitor. The fly screen can provide hit compounds that otherwise might not be discovered because the target, in this case G12V kRAS, is presented for targeting in its natural state. Also, compounds active in the fly must also be bioavailable when administered in the food, and toxic compounds will most likely prevent the development of the flies, and, therefore, will not register as hits. The present disclosure describes use of the kRAS fly screen to identify a class compounds of interest as anti-kRAS agents based on a core chemical scaffold.

SUMMARY

Pyrazolopyrimidine RAS modulating compounds and methods of using the same are provided. The pyrazolopyrimidine compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

DEFINITIONS

Figure 1:
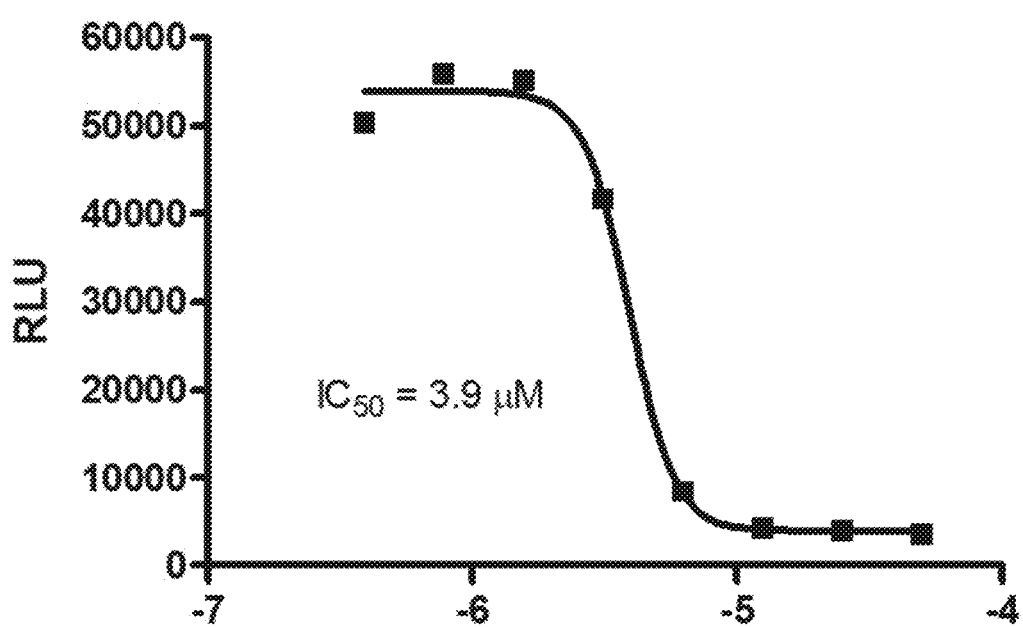
FIG. 1, Cytotoxicity of exemplary compound (Structure 1) on SW620 human cancer cells. The cytotoxicity of compounds of interest are tested against the human colon cancer cell line SW620 as described in the experimental section. SW620 cells express a mutant G12V kRAS. Compounds are incubated with cells for 72 hours and the assay developed using Cell Titer Glo 2.0. $IC_{50}$ values are determined using GraphPad Prism4. Exemplary compound Structure 1 was determined to have an $IC_{50}$ of 3.9γM in the assay.

Unless defined otherwise, all technical and scientific terms used herein have the same meaning as is commonly understood by one of skill in the art to which this invention belongs. All patents and publications referred to herein are incorporated by reference. As used in the specification and claims, the singular form "a", "an" and "the" include plural references unless the context clearly dictates otherwise.

AKT is the serine/threonine kinase. AKT (also known as protein kinase B or PKB) has become a major focus of attention because of its critical role in regulating diverse cellular functions including metabolism, growth, proliferation, survival, transcription and protein synthesis.

Alkyl by itself or as part of another substituent refers to a monovalent saturated aliphatic hydrocarbon group. This term includes linear, cyclic, or branched groups or a combination thereof. The group can have the number of carbon atoms designated (e.g., C1-C8 means one to eight carbon atoms). In some cases, an alkyl group has from 1 to 10 carbon atoms, such as 1 to 6 carbon atoms, or 1 to 5, or 1 to 4, or 1 to 3 carbon atoms. Examples of alkyl groups include, but are not limited to, methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Structures for a few exemplary alkyl groups are provided in Table 1 below.

Alkenyl refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

Aryl or Ar refers to a polyunsaturated, aromatic hydrocarbon group having a single ring (bicyclic) or multiple rings (preferably bicyclic) which can be fused together or linked covalently. In some cases, an Aryl group has 6 to 18 carbon atoms, such as 6-10 carbon atoms having a single ring (such as is present in a phenyl group) or a ring system having multiple condensed rings (examples of such aromatic ring systems include naphthyl, anthryl and indanyl) which condensed rings may or may not be aromatic, provided that

TABLE 1

Structure of exemplary alkyl groups

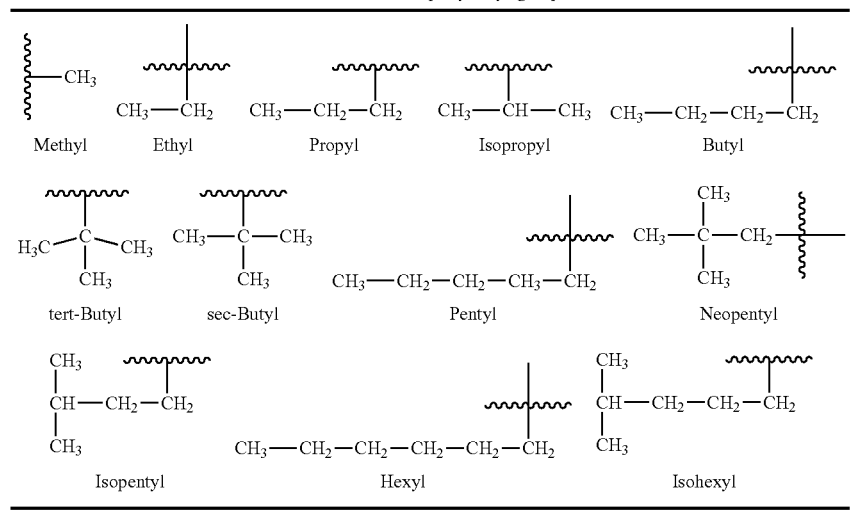

Alkyl groups can be substituted or unsubstituted, unless otherwise indicated.

The term "substituted alkyl" refers to an alkyl group as defined herein wherein one or more carbon atoms in the alkyl chain have been optionally replaced with a heteroatom such as O—, N—, S—, —(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocloooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO2-alkyl, —SO2-aryl, SO2-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic. Examples of substituted alkyl include haloalkyl, thioalkyl, aminoalkyl, and the like.

the point of attachment is through an atom of an aromatic ring. Examples of aryl groups include, but are not limited to, phenyl and naphthalene-1-yl, naphthalene-2-yl, biphenyl and the like. Aryl groups can be substituted or unsubstituted, unless otherwise indicated. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. The structures of a few exemplary aryl groups are provided in Table 2 below.

TABLE 2

Examples of aryl groups

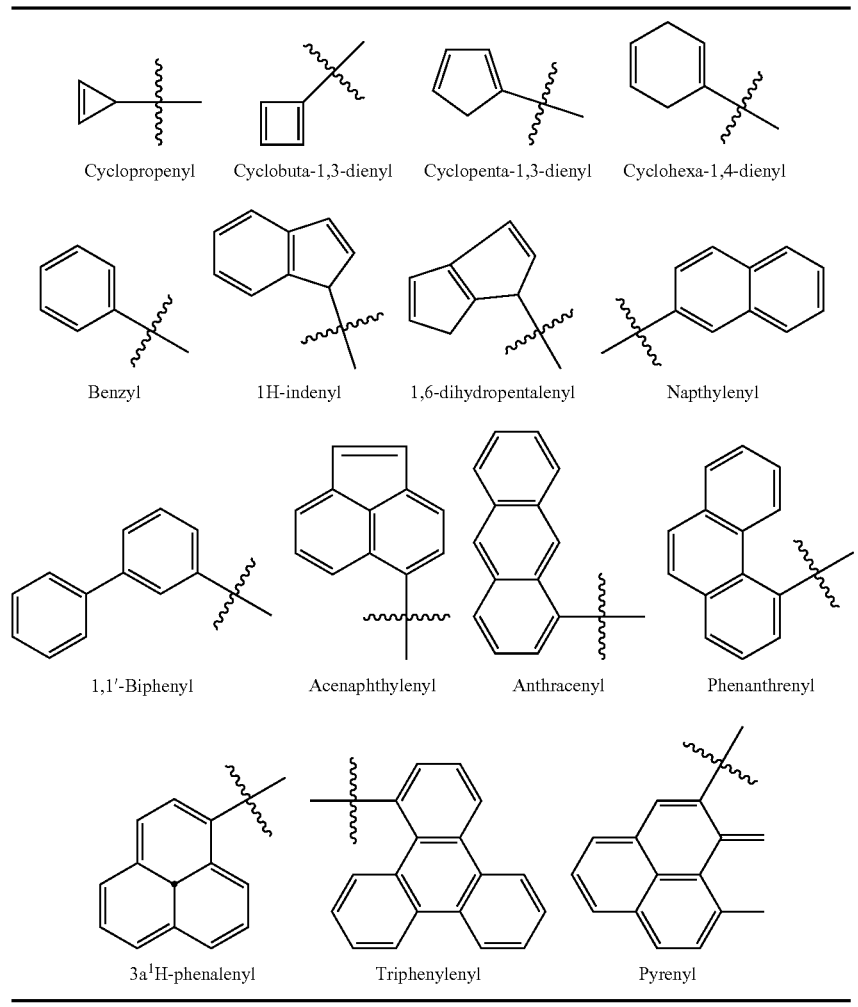

DURAS is diverse RAS, which is a distinct branch of the functionally diverse RAS superfamily of monomeric GTPases.

DMEM is Dulbecco's Modified Eagle Medium. It is a modification of Basal Medium Eagle (BME) that contains a four-fold higher concentration of amino acids and vitamins, as well as additional supplementary components. The original DMEM formula contains 1000 mg/L of glucose and was first reported for culturing embryonic mouse cells.

Effective amount or therapeutically effective amount refers to an amount of a compound enough to affect the intended application, such as an amount enough to treat a specified disorder or disease or one or more of its symptoms and/or to prevent the occurrence of the disease or disorder. The therapeutically effective amount may vary depending upon the intended treatment application (e.g., in vivo), or the subject and disease condition being treated, e.g., the weight and age of the subject, the severity of the disease condition, the manner of administration and the like, which can readily be determined by one of ordinary skill in the art.

Enantiomer. Enantiomers are stereoisomers that are non-superimposable mirror images. A molecule with 1 chiral carbon atom exists as 2 stereoisomers termed enantiomers. Enantiomers differ in their configuration (R or S) at the stereogenic center.

ERAS is RAS expressed by ES cells. This is a constitutively active member of the small GTPase RAS protein family. The encoded protein activates the phosphatidylinositol 3-kinase signal transduction pathway in undifferentiated stem cells but is not expressed in differentiated cells. This gene may be involved in cancer and chemotherapy resistance.

ERK is extracellular-signal-regulated kinase which is a widely expressed protein kinase and intracellular signaling molecules involved in functions including the regulation in GEM is GTP binding protein overexpressed in skeletal muscle. The protein belongs to the RAD/GEM family of GTP-binding proteins. It is associated with the inner face of the plasma membrane and could play a role as a regulatory protein in receptor-mediated signal transduction. Alternative splicing occurs at this locus and two transcript variants encoding the same protein have been identified.

G Domain is a highly conserved domain common to all GTPases that is located on the largest of the G proteins three subunits, the α unit. The two smaller subunits are the β and γ units.

GTPase refers to a large family of hydrolase enzymes that bind and hydrolyze GTP.

Halo or halogen, by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include, but are not limited to, 1-chloroethyl, 3-bromopropyl, trifluoromethyl and the like.

Heterocyclyl refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Heterocyclic groups can be monocyclic or can be fused or linked covalently to an aryl or heteroaryl ring system.

Heteroaryl refers to an aromatic group containing at least one heteroatom. Examples include, but are not limited to, pyridyl, pyridazinyl, pyrazinyl, pyrimidinyl, triazinyl, guinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl groups can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. The structures of a few exemplary heterocyclyls are shown in Table 3.

TABLE 3

Examples of heterocyclyls

| 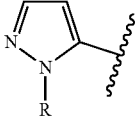 | 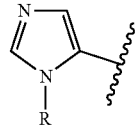 | 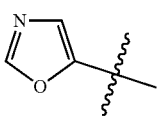 | 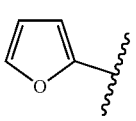 |
|---|---|---|---|
| Substituted Pyrazolyl | Substituted Imidazole | Oxazolyl | Furanyl |
| 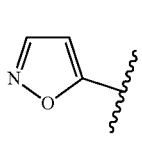 | 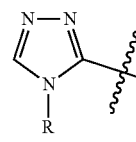 | 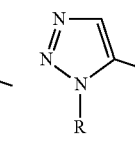 | 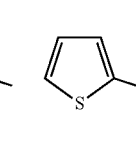 |
| Isoxazolyl | Substituted 1,2,4 Triazolyl | Substituted 1,2,3 Triazolyl | Thiophenyl |
| 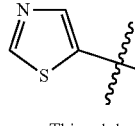 | 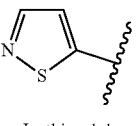 | 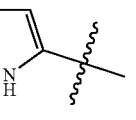 | 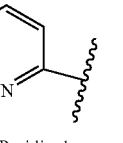 |
| Thiazolyl | Isothiazolyl | Pyrrolyl | Pyridinyl |
| 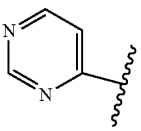 | 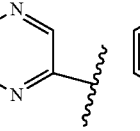 | 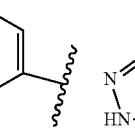 | 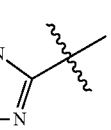 |
| Pyrimidinyl | Pyrazinyl | Pyranyl | Tetrazolyl |

Substituents of interest for substituted alkyl, substituted alkenyl, and substituted alkynyl groups include, but are not limited to, halogen, —CN, —CO$_2$R', —C(O)R', —C(O)NR'R", oxo (=O), —OR', —OC(O)R', —OC(O)NR'R"— NO$_2$, —NR'C(O)R', —NR'''C(O)NR'R", —NR'R", —NRCO$_2$R", —NR'S(O)$_2$R''', —SR', —S(O)R", —S(O)$_2$R', —S(O)$_2$NR'R", —SiR'R" R''', —N$_3$, substituted or unsubstituted $C_{6-10}$ aryl, substituted or unsubstituted 5- to 10-membered heteroaryl, and substituted or unsubstituted 3- to 10-membered heterocyclyl, in a number ranging from zero to (2m'+1), where m' is the total number of carbon atoms in such radical.

Substituents of interest for substituted aryl, substituted heteroaryl and substituted heterocyclyl groups include, but are not limited to, halogen, —CN, —CO$_2$R', —C(O)R', —C(O)NR'R", oxo, —OR', —OC(O)R', —OC(O)NR'R", —NO$_2$, —NRC(O)R", —NR'C(O)NR"R'", —NR'R", —NR'CO$_2$R", —NR'S(O)$_2$R", —SR', —S(O)R', —S(O)$_2$R', —S(O)$_2$NR'R", —NR'—C(NHR").dbd.NR'", —SiR'R"R'", —N$_3$, substituted or unsubstituted $C_{1-8}$ alkyl group, substituted or unsubstituted $C_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system. As used above, R', R" and R'" each independently refer to a variety of groups including hydrogen, substituted or unsubstituted $C_{2-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

kDa is kilo Dalton. Dalton is the standard unit that is used for indicating mass on an atomic or molecular scale.

Linker/Linkage. The term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone.

MEK, mitogen-activated protein kinase also known as MAP2K, MEK, MAPKK, is a kinase enzyme which phosphorylates mitogen-activated protein kinase (MAPK).

MET, methyl, is a chemical group with a structure CH$_3$—.

MRAS is muscle RAS oncogene homolog. This gene encodes a member of the RAS family of small GTPases. These membrane-associated proteins function as signal transducers in multiple processes including cell growth and differentiation, and dysregulation of RAS signaling has been associated with many types of cancer. The encoded protein may play a role in the tumor necrosis factor-alpha and MAP kinase signaling pathways. Alternatively, spliced transcript variants encoding multiple isoforms have been observed for this gene.

NKIRAS is NFκB inhibitor interacting RAS-like. Among its related pathways are NF-KappaB Family Pathway and TNF-alpha/NF-kB Signaling Pathway. It is also related to GTP binding and GTPase activity.

NSCLC is non-small-cell lung carcinoma. NSCLC is any type of epithelial lung cancer other than small cell lung carcinoma. As a class, NSCLCs are relatively insensitive to chemotherapy, compared to small cell carcinoma. When possible, they are primarily treated by surgical resection with curative intent, although chemotherapy is increasingly being used both pre-operatively and post-operatively.

Pharmaceutically acceptable carrier, diluent, or excipient is a carrier, diluent, or excipient compatible with the other ingredients of the formulation and not deleterious to the recipient thereof.

Pharmaceutically acceptable salt refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the substituents found on the compounds described herein. When compounds of the present disclosure contain relatively acidic functionalities, base addition salts can be obtained by contacting the neutral form of such compounds with enough of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with enough of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galacturonic acids and the like. Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

PI3K is phosphatidylinositol-4,5-bisphosphate 3-kinase. PI3K(s) are a family of enzymes involved in cellular functions such as cell growth, proliferation, differentiation, motility, survival and intracellular trafficking, which in turn are involved in cancer.

RAF are a family of three serine/threonine-specific protein kinases that are related to retroviral oncogenes. RAF kinases participate in the RAS-RAF-MEK-ERK signal transduction cascade, also referred to as the mitogen-activated protein kinase (MAPK) cascade. Activation of RAF kinases requires interaction with RAS-GTPases. The three RAF kinase family members are: A-Raf, B-Raf and C-Raf (Raf-1).

Rad is the prototypic member of a class of Ras-related GTPases.

Radiation therapy means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including x-rays, gamma rays and neutrons.

RAL is RAS-related protein ral. Ral protein family, including RALA and RALB, belongs to the RAS family of small GTPases. Like other RAS GTPases, Ral proteins function as molecular switches alternating between inactive GDP-bound and active GT-bound states.

RAP is GTP-binding protein also known as RAS-related proteins or simply RAP is a type of small GTPase, similar in structure to RAS. These proteins share approximately 50% amino acid identity with the classical RAS proteins and have numerous structural features in common. The most striking difference between RAP proteins and RAS proteins resides in their 61st amino acid: glutamine in RAS is replaced by threonine in RAP proteins. RAP counteracts the mitogenic function of RAS because it can interact with RAS GAPs and RAF in a competitive manner.

RAS refers to a family of related proteins which are ubiquitously expressed in all cell lineages and organs. All RAS protein family members belong to a class of protein called small GTPase that are involved in transmitting signals within cells. RAS proteins are a type of G-protein found in the cytosol that are homologous to the alpha subunit of heterotrimeric G-proteins, but unlike the alpha subunit of G proteins, a small GTPase can function independently as a hydrolase enzyme to bind to and hydrolyze a guanosine triphosphate (GTP) to form guanosine diphosphate (GDP). RAS proteins of interest include, but are not limited to hRAS, kRAS and nRAS.

REM1/REM2 is RAS (RAD and GEM)—like GTP-binding 1. The proteins are expressed in endothelial cells, where they promote reorganization of the actin cytoskeleton and morphological changes in the cells.

RERG is RAS-related and estrogen-regulated growth inhibitor. RERG, a member of the RAS superfamily of GTPases, inhibits cell proliferation and tumor formation.

SALT THEREOF refers to a compound formed when the hydrogen of an acid is replaced by a cation, such as a metal cation or an organic cation and the like. In some cases, the salt is a pharmaceutically-acceptable salt, although this is not required for salts of intermediate compounds which are not intended for administration to a patient.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Signal transduction is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

SOS (Son of Sevenless) refers to guanine nucleotide exchange factor that act on RAS proteins and catalyzes the exchange of guanosine diphosphate (GDP) with guanosine triphosphate (GTP).

TREATING or TREATMENT as used herein refers to the treating or treatment of a disease or medical condition (such as a bacterial infection) in a patient, such as a mammal (particularly a human or a companion animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present disclosure can exist in unsolvated forms as well as solvated forms, including hydrated forms. In general, both solvated forms and unsolvated forms are intended to be encompassed within the scope of the present disclosure. Certain compounds of the present disclosure may exist in multiple crystalline or amorphous forms (i.e., as polymorphs). In general, all physical forms are equivalent for the uses contemplated by the present disclosure and are intended to be within the scope of the present disclosure.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. Enantiomeric and stereoisomeric mixtures can be resolved into their component enantiomers or stereoisomers using separation techniques or chiral synthesis techniques well known to the skilled artisan. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the subject compounds may be radiolabeled with radioactive isotopes, such as for example tritium, iodine-$^{125}$I or $^{14}$C. Examples of isotopes that can be incorporated into the compounds disclosed herein include, but are not limited to, $^{2}$H, $^{3}$H, $^{11}$C, $^{13}$C, $^{14}$C, $^{15}$N, $^{18}$O, $^{17}$O, etc. All isotopic variations of the subject compounds, whether radioactive or not, are intended to be encompassed within the scope of the present disclosure.

Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

TP is total protein. A total serum protein test measures the total amount of protein in the blood. It also measures the amounts of two major groups of proteins in the blood: albumin and globulin.

$V_z$ is apparent volume of distribution during terminal phase, theoretical volume in which a drug is distributed.

When describing the compounds, compositions, methods and processes of this invention, the following terms have the meanings defined herein, unless otherwise indicated.

DETAILED DESCRIPTION

As summarized above, RAS modulating compounds and methods of using the same are provided. The compounds find use in modulating the activity of a target RAS in a sample. The target RAS can be a mutant RAS that is implicated in a condition or disease. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

Before the present invention is described in greater detail, it is to be understood that this invention is not limited to particular embodiments described, as such may, of course, vary. It is also to be understood that the terminology used herein is for the purpose of describing embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Modulation of RAS

The present disclosure provides RAS modulating compounds and salts thereof, and solvate, hydrate and/or prodrug form thereof, and compositions including the same. Also provided are methods that find use in the modulation of the activity of a target RAS GTPase. As used herein, the terms "RAS" and "RAS GTPase" are used interchangeably to refer to members of the class of hydrolase enzymes called, also called "small GTPase", that are involved in transmitting signals within cells. RAS subfamily members of interest which may be targeted using the subject compounds include, but are not limited to, hRAS, kRAS and nRAS. In some cases, the target RAS is one that is implicated in a cancer of interest. Exemplary target RAS proteins of interest which may be targeted using the subject compounds include, but are not limited to, DIRAS1; D1RAS2; DIRAS3; ERAS; GEM; MRAS; NKIRAS1; NKIRAS2; nRAS; RALA; RALB; RAP1A; RAP IB; RAP2A; RAP2B; RAP2C; RASD1; RASD2; RASL10A; RASL10B; RASL11A; RASL11B; RASL12, REM1; REM2; RERG; RERGL; RRAD; RRAS; RRAS2.

Modulation of RAS GTPase activity can include partial or full blockage of the Ras-Raf-MEK-ERK pathway (MAPK pathway) to result in modulation of cell proliferation. The subject compounds may modulate RAS GTPase activity by inhibiting the interaction of RAS with its upstream effectors that mediate the exchange of GDP for GTP such as SOS or its downstream effectors such as the RAF kinases. In some embodiments the subject compounds modulate synthetic lethal targets down stream of RAS resulting in loss of RAS function and cell death. In some embodiments the synthetic lethal targets are components of mitochondrial electron transport chain, such as Complex I.

The target RAS can be a RAS GTPase or a mutant RAS GTPase which is implicated in a disease condition (e.g., as described herein). In some cases, the target RAS is a mutant RAS GTPase, such as a hRAS, a nRAS or a kRAS mutant. The mutant RAS can include a mutation at a variety of positions, such as mutation at G12, G13 or Q61. In certain cases, the RAS is a RAS-G12V mutant. The present disclosure provides RAS modulating compounds that can have anti-cancer activity. The subject compounds can interfere with the interaction of mutant RAS GTPases with their upstream and downstream targets thereby inhibiting proliferation of cancer cells.

In further describing the various aspects of the invention, the function and structure of various embodiments of RAS modulating compounds are described first in greater detail, followed by a description of methods and applications in which the compounds find use.

Compounds that Modulate RAS Activity

As summarized above, aspects of the present disclosure include RAS modulating compounds. The RAS modulating compounds are compounds which modulate the activity of a target RAS GTPase in a sample upon contact with a sample or components thereof. In some cases, by modulating the activity of a target RAS GTPase is meant that an activity related to the RAS in a cell is inhibited by 10% or more, such as 20% or more, 30% or more, 40% or more, 50% or more, 60% or more, 70% or more, 80% or more, 90% or more, or even more relative to a control, e.g., a cell not contacted with the compound of interest. Any convenient methods can be utilized in assessing modulation of the activity of RAS in a sample. In some cases, modulation of the activity of the target RAS may be assessed by observing a signal of the Ras-Raf-MEK-ERK pathway. Modulation of the signals and activities of the Ras-Raf-MEK-ERK pathway can be assessed using any convenient methods, such as those described by Kato-Stankiewicz et al. (Inhibitors of RAS/Raf-1 interaction identified by two-hybrid screening revert RAS-dependent transformation phenotypes in human cancer cells. Proc Natl Acad Sci USA. 2002; 99: 14398-403) and assays described in the Examples section herein, e.g., a phosphorylated ERK bioassay and cell morphology assay. In some instances, the types of cells in which the subject compounds exhibit activity are ones that include a mutant RAS of interest.

The sample can include a cell which includes the target RAS GTPase. In some embodiments, the RAS modulating compound decreases RAS-induced proliferation of cells that include the RAS GTPase. In some cases, the RAS-induced cellular proliferation is induced by a mutant RAS that can be targeted for inhibition using the subject compounds. By "decreases RAS-induced proliferation" is meant decreasing proliferation of the cells by 10% or more, such as 20% or more, 30% or more, 40% or more, 50% or more, 60% or more, 70% or more, 80% or more, 90% or more, or even more, relative to a control, e.g., cells not contacted with the compound of interest.

In certain embodiments, the RAS modulating compounds modulate the interaction of an activated GTP-bound RAS with a downstream protein target of the pro-growth Ras-Raf-MEK-ERK pathway. In some cases, the RAS modulating compound modulates the interaction of an activated GTP-bound RAS of interest with a RAF family protein. In certain instances, the activated GTP-bound RAS is a mutant RAS such as a hRAS, nRAS or kRAS mutant. In certain instances, the RAS modulating compound is an inhibitor of kRAS, such as a specific inhibitor of a mutated kRAS variant. The subject compound can provide a significant anti-cancer effect in patients suffering a malignancy.

Structural Features

The RAS modulating compound can have a core 5-6 fused bicyclic ring system including a 5 membered ring fused to a 6 membered ring. The 5-6 fused bicyclic ring system can be aromatic, unsaturated or saturated. The 6- and 5-membered rings can be independently carbocyclic or heterocyclic. Each ring can include 1-3 heteroatoms, such as N heteroatoms arranged in any convenient configuration to provide a core ring system upon which substituents of interest can be appended. 5-6 fused bicyclic ring systems of interest which may be adapted to use in the subject compounds include, but are not limited to, pyrazolopyrimidine, imidazopyrimidine and triazolopyrimidine. As used herein, the term "pyrazolopyrimidine compound" is used to describe compounds having a pyrazolopyrimidine core ring system and analog compounds thereof which may include one additional N atom or one fewer N atom, in comparison to the core 5-6 fused bicyclic ring system of the parent compound.

The 5-6 fused bicyclic ring system of the RAS modulating compounds can be substituted with two, three, four or more substituent groups. In certain cases, to the 6-membered ring is appended two substituent groups and to the 5-membered is appended one substituent group. In some instances, the RAS modulating compound includes 2 or 3 substituent groups independently selected from aryl-alkyl, substituted aryl-alkyl, heteroaryl-alkyl, substituted heteroaryl-alkyl, aryl, substituted aryl, heteroaryl and substituted heteroaryl. In some cases, the 2 or 3 substituent groups are independently selected from phenyl-methylene, substituted phenyl-methylene, pyridyl-methylene, substituted pyridyl-methylene, phenyl, substituted phenyl, pyridyl and substituted pyridyl. The 6-membered ring can be further substituted with amino, substituted amino, heterocycle or substituted heterocycle.

In some embodiments, the RAS modulating compound is of formula (B):

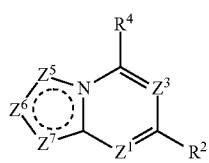

(B)

wherein:

$Z^1$ is N or $CR^1$;

$Z^3$ is N or $CR^3$;

$Z^5$ is N, $CR^5$ or $NR^5$;

$Z^6$ is N, $CR^6$ or $NR^6$; and $Z^7$ is N, $CR^7$ or $NR^7$; and $R^1$-$R^7$ are independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino, and/or wherein any two ortho $R^1$-$R^7$ groups can be cyclically linked to provide an ortho-fused 5-membered carbocyclic or heterocyclic ring optionally further substituted;

or a salt thereof, or a solvate, hydrate or prodrug form thereof.

In some embodiments of formula (B), $Z^9$ is N:

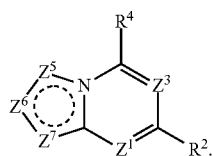

In embodiments of formula (B), the compound is of formula (B1):

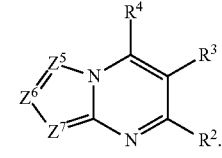

(B1)

In some embodiments of formula (B1), $Z^1$ is N. In some embodiments of formula (B1), $Z^1$ is $CR^1$. In some instances of formula (B1), $Z^3$ is N. In some instances of formula (B1), $Z^3$ is $CR^3$. In some cases of formula (B1), $Z^5$ is N. In some cases of formula (B1), $Z^5$ is $CR^5$. In some embodiments of formula (B1), $Z^6$ is N. In some embodiments of formula (B1), $Z^6$ is $CR^6$. In some instances of formula (B1), $Z^7$ is N. In some instances of formulae (B1)-(B2), $Z^7$ is $CR^7$.

In some cases of formula (B1), the compound is of formula (B1.1):

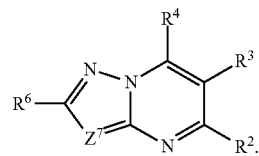

(B1.1)

In some embodiments of formula (B1.1), $Z^7$ is N. In some embodiments of formulae (B1.1), $Z^7$ is $CR^7$. In some embodiments of formula (81.1), $Z^6$ is N. In some embodiments of formula (B1.1), $Z^6$ is $CR^6$. In some embodiments of formula (B1.1), $Z^5$ is $CR^5$. In some embodiments of formula (B1.1), $Z^5$ is N. In some embodiments of formula (B1.1), the compound is of formula (B1.1a):

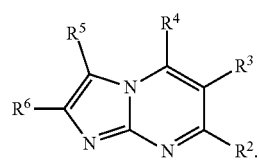

(B1.1a)

In some embodiments of formula (B1.1a), $Z^7$ is N. In some embodiments of formula (B1.1a), $Z^7$ is $CR^7$. In some embodiments of formula (B1.1), the compound is of formula (B1.1b):

(B1.1b)

In some cases of formula (B1.1a)-(B1.1c), $R^2$-$R^7$ are independently selected from H, alkyl, substituted alkyl, aryl, substituted aryl, heteroaryl, substituted heteroaryl, heterocycle, substituted heterocycle, alkoxy, substituted alkoxy, alkylamino and substituted alkylamino. In some cases of formula (B1.1a) and (B1.1c), $R^7$ is selected from aryl, substituted aryl, heteroaryl and substituted heteroaryl (e.g., phenyl, substituted phenyl, pyridyl or substituted pyridyl).

In some instances of formula (B1.1a)-(B1.1c), $R^3$ is selected from aryl-alkyl, substituted aryl-alkyl, heteroaryl-alkyl and substituted heteroaryl-alkyl. In certain cases, $R^3$ is selected from aryl-C1-6alkyl, substituted aryl-C1-6alkyl, heteroaryl-C1-6alkyl and substituted heteroaryl-C1-6alkyl.

In some instances of formula (B1.1a), $R^3$ is selected from phenyl-methylene-, substituted phenyl-methylene-, pyridyl-methylene-, substituted pyridyl-methylene-; and $R^7$ is selected from phenyl, substituted phenyl, pyridyl and substituted pyridyl.

In some instances of formula (B1.1a)-(B1.1c), $R^3$ is selected from aryl, substituted aryl, heteroaryl and substituted heteroaryl. In certain instances of formula (B1.1a)-(B1.1c), $R^3$ is selected from H, alkyl and substituted alkyl. $R^2$ can be selected from aryl-alkyl, substituted aryl-alkyl, heteroaryl-alkyl and substituted heteroaryl-alkyl. In some cases, $R^2$ is selected from aryl, substituted aryl, heteroaryl and substituted heteroaryl. $R^2$ can be selected from phenyl, substituted phenyl, pyridyl and substituted pyridyl. In some instances of formula (B1.1a)-(B1.1c), $R^2$ is selected from H, alkyl and substituted alkyl.

In some instances of formula (B1.1a)-(B1.1b), $R^6$ is selected from aryl, substituted aryl, heteroaryl and substituted heteroaryl. $R^6$ can be selected from phenyl, substituted phenyl, pyridyl and substituted pyridyl. In some cases, $R^2$ is selected from aryl, substituted aryl, heteroaryl and substituted heteroaryl. $R^2$ can be selected from phenyl, substituted phenyl, pyridyl and substituted pyridyl.

In some instances of formula (B1.1a)-(B1.1b), $R^2$, $R^4$ and $R^6$ are independently selected from aryl, substituted aryl, heteroaryl and substituted heteroaryl. $R^2$, $R^4$ and $R^6$ can be independently selected from phenyl, substituted phenyl, pyridyl and substituted pyridyl.

In some instances of the embodiment of formulae (B1.1a)-(B1.1c) described herein, $R^4$ is —NR$^{25a}$R$^{25b}$; and R$^{25a}$ and R$^{25b}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or R$^{25a}$ and R$^{25b}$ are cyclically linked and together with the N atom through which they are connected provide a 5 or 6-membered heterocycle that is optionally further substituted.

In some cases of formula (B1.1a) and (B1.1b), $R^3$, $R^5$ and/or $R^7$ are each H. In some instances of formula (B1.1a) and (B1.1b), $R^2$, $R^4$ and $R^6$ are independently selected from aryl, substituted aryl, heteroaryl and substituted heteroaryl. In certain instances of formula (B1.1a) and (B1.1b), $R^2$, $R^4$ and $R^6$ are independently selected from phenyl, substituted phenyl, pyridyl and substituted pyridyl. In some embodiments of formulae (B1.1a) and (B1.1b), the compound is of one of the formulae:

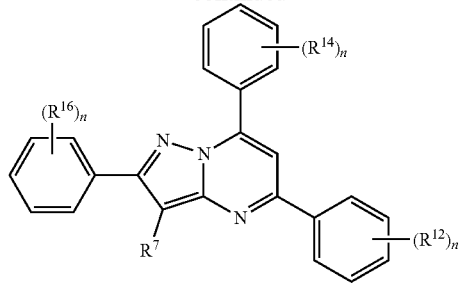

-continued

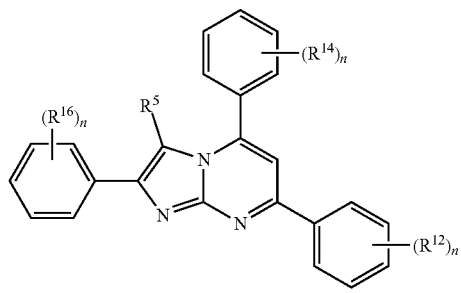

wherein:

each $R^{12}$, $R^{14}$ and $R^{16}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

each n is independently 0-5; and $R^5$ and $R^7$ are independently H, alkyl or substituted alkyl. In certain instances, $R^5$ or $R^7$ is H. In certain cases, $R^5$ or $R^7$ is C (1-6) alkyl or substituted C (1-6) alkyl, such as methyl. In some embodiments, each $R^{12}$, each $R^{14}$ and each $R^{16}$, if present, is independently selected from halogen, C (1-6) alkyl, substituted C (1-6) alkyl, C (1-6) alkoxy and substituted C (1-6) alkoxy.

In some embodiments of formulae (B1.1a) and (B1.1b), the compound has one of the following structures:

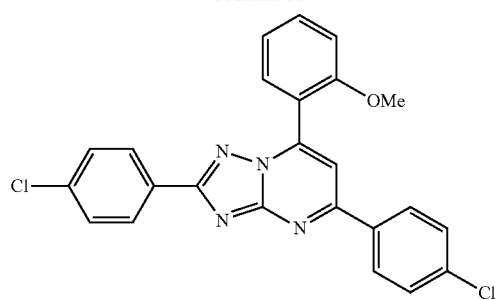
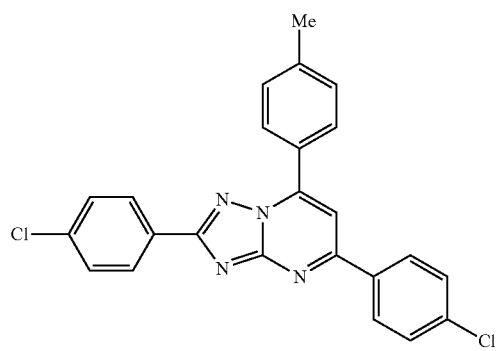
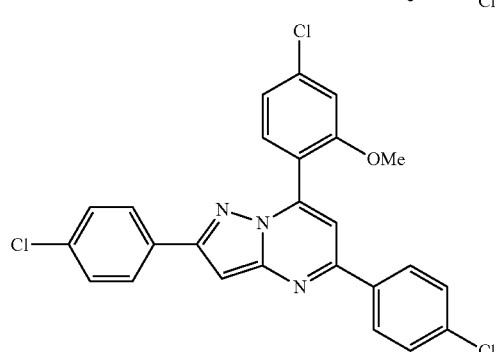
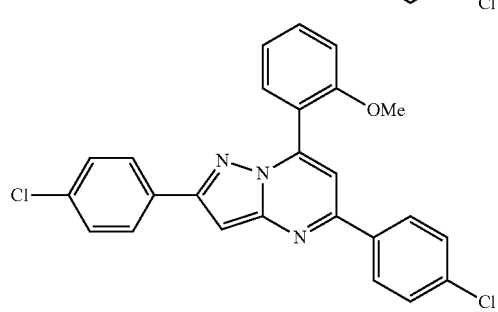
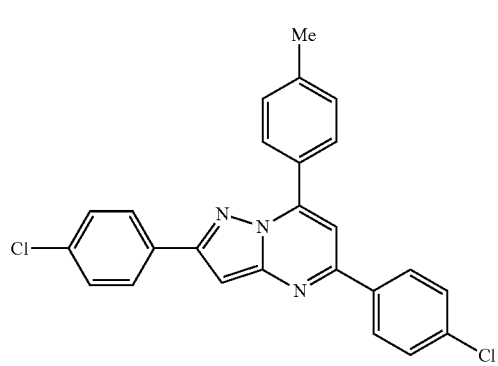

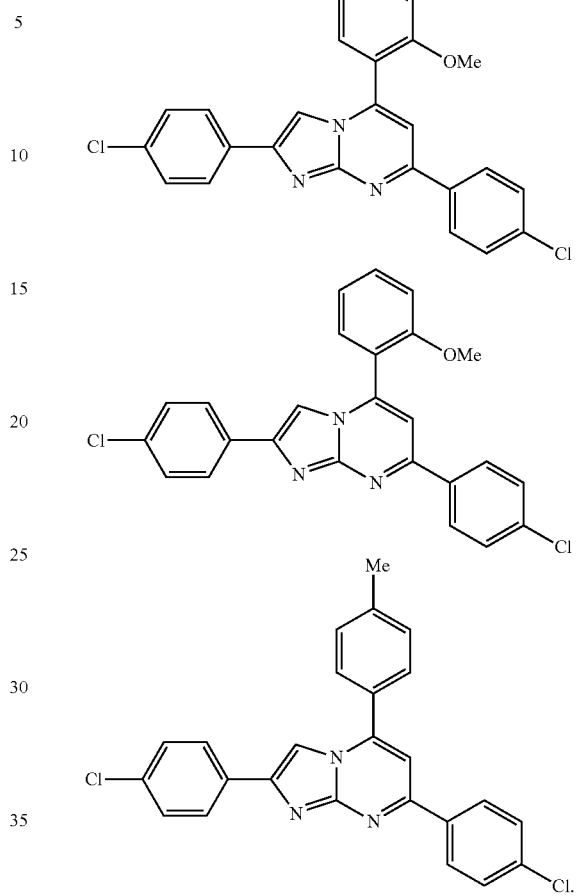

In some embodiments of formulae (B1.1), the compound is of formula (B1.1c):

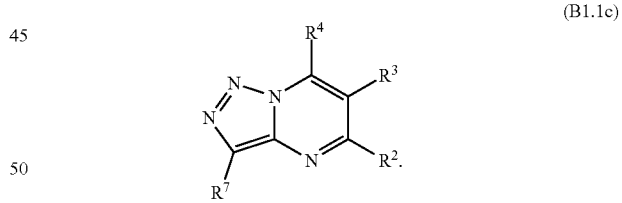

(B1.1c)

In some cases of formulae (B1.1c) and (B1.1a), $R^3$ and/or $R^5$ are each H. In some instances of formulae (B1.1c) and (B1.1a), $R^7$ is selected from aryl, substituted aryl, heteroaryl and substituted heteroaryl. In certain instances of formulae (B1.1c) and (B1.1a), $R^7$ is selected from phenyl, substituted phenyl, pyridyl and substituted pyridyl. In some instances of formulae (B1.1c) and (B1.1a), $R^2$, $R^4$ and $R^7$ are independently selected from aryl, substituted aryl, heteroaryl and substituted heteroaryl. In certain instances of formulae (B1.1c) and (81.1a), $R^2$, $R^4$ and $R^7$ are independently selected from phenyl, substituted phenyl, pyridyl and substituted pyridyl.

In some embodiments of formulae (B1.1a) and (B1.1c), the compound is of one of the following structures:

23

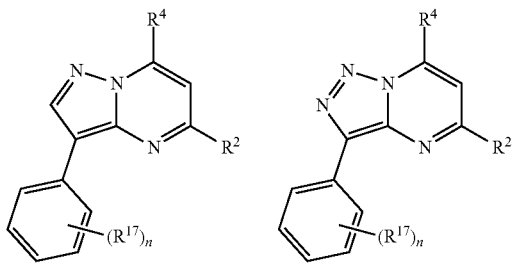

wherein:
each $R^{17}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
n is 0-5; and
$R^5$ is H, alkyl or substituted alkyl. In some embodiments, $R^2$ and $R^4$ are independently selected from phenyl, substituted phenyl, pyridyl and substituted pyridyl.

In some embodiments of formula (B1.1a) and (B1.1c),
$R^7$ is phenyl, substituted phenyl, pyridyl or substituted pyridyl;
$R^2$ is H, alkyl or substituted alkyl;
$R^4$ is —$NR^{25a}R^{25b}$; and
$R^{25a}$ and $R^{25b}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or $R^{25a}$ and $R^{25b}$ are cyclically linked and together with the N atom through which they are connected provide a 5 or 6-membered heterocycle that is optionally further substituted. In some instances, $R^{25a}$ and $R^{25b}$ are cyclically linked to provide a pyrrolidine, imidazolidine, pyrazolidine, oxazolidine, isoxazolidine, piperidine, piperazine or morpholine ring, which ring is optionally further substituted, e.g., with one or more groups selected from alkyl, substituted alkyl, alkoxy, substituted alkoxy, hydroxy, and the like. In some embodiments of formulae (B1.1a) and (B1.1c), each $R^{23}$ is independently selected from H, C1-6alkyl, substituted C1-6alkyl, C1-6alkoxy, substituted C1-6alkoxy and halogen.

In some embodiments of formulae (B1.1a) and (B1.1c), the compound has one of the following structures:

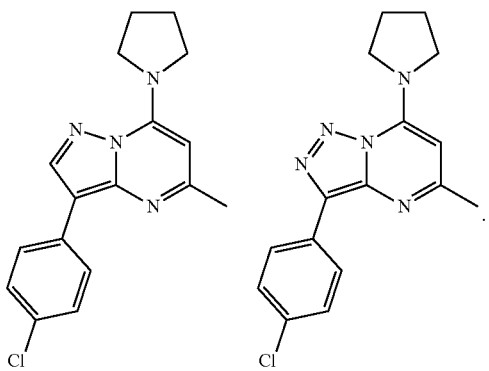 [SMILES: Cc1cc(N2CCCC2)n2ncc(-c3ccc(Cl)cc3)c2n1 ; Cc1cc(N2CCCC2)n2nnc(-c3ccc(Cl)cc3)c2n1]

In some embodiments of formula (B1.1a), the compound is of the formula:

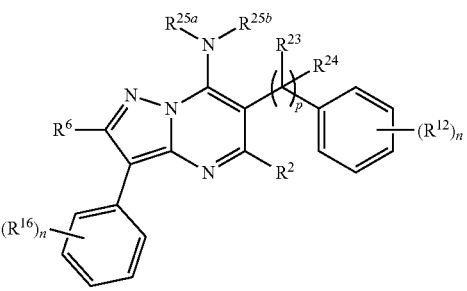

wherein:
each $R^{12}$ and $R^{16}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
p is 0-3 (e.g., 0, 1 or 2);
each n is independently 0-5;
$R^{25a}$ and $R^{25b}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or $R^{25a}$ and $R^{25b}$ are cyclically linked and together with the N atom through which they are connected provide a 5 or 6-membered heterocycle that is optionally further substituted; and
$R^{23}$ and $R^{24}$ are independently selected from H, alkyl and substituted alkyl or $R^{23}$ and $R^{24}$ are cyclically linked to provide a cycloalkyl or substituted cycloalkyl ring.

In certain instances of the formula, $R^{25a}$ is H, alkyl or substituted alkyl and $R^{25b}$ is selected from alkyl, substituted alkyl, aryl, substituted aryl, heteroaryl, substituted heteroaryl. In some cases, $R^{25b}$ is substituted alkyl, such as aryl-C1-6alkyl-, substituted aryl-C1-6alkyl-, heteroaryl-C1-6alkyl- or substituted heteroaryl-C1-6alkyl-. In some cases, $R^{25b}$ is selected from phenyl-C1-6alkyl-, substituted phenyl-C1-6alkyl-, pyridyl-C1-6alkyl- and substituted pyridyl-C1-6alkyl-. In certain instances, $R^{25a}$ is H, alkyl or substituted alkyl and $R^{25b}$ is pyridyl-methylene or substituted pyridyl-methylene.

In some embodiments of formula (B1.1a), the compound is of the formula:

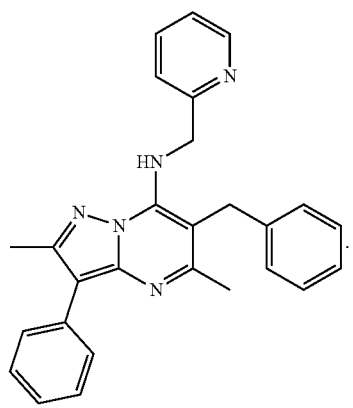 [SMILES: Cc1nc2c(-c3ccccc3)c(C)nn2c(NCc2ccccn2)c1Cc1ccccc1]

In some embodiments of formula (B1.1a), the compound is of the formula:

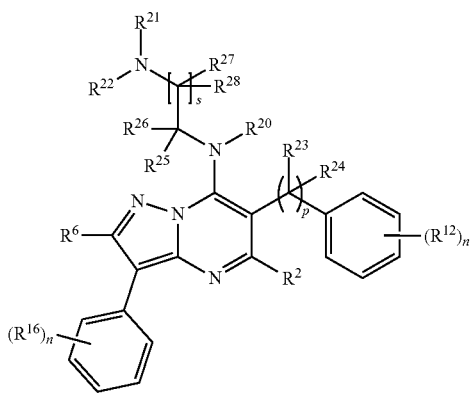

wherein:

each $R^{12}$ and $R^{16}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

s is 0-5 (e.g., s is 1-5 or 1-4, such as 1, 2 or 3) and p is 0-3 (e.g., 0; 1 or 2); each n is independently 0-5;

$R^{21}$ and $R^{22}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or $R^{21}$ and $R^{22}$ are cyclically linked and together with the N atom through which they are connected provide a 5 or 6-membered heterocycle that is optionally further substituted;

$R^{23}$ and $R^{24}$ are independently selected from H, alkyl and substituted alkyl or $R^{23}$ and $R^{24}$ are cyclically linked to provide a cycloalkyl or substituted cycloalkyl ring; and $R^{25}$ to $R^{26}$ are each independently selected from H, D, halogen (e.g., F), alkyl and substituted alkyl. In certain instances, $R^{25}$ to $R^{28}$ are selected from D and F. In certain instances, $R^{25}$ and $R^{26}$ are each C(1-6)alkyl, such as methyl. In certain instances, $R^{25}$ and $R^{26}$ are each halogen, such as fluoro. In certain instances, $R^{25}$ and $R^{26}$ are each H. In certain instances, $R^{25}$ and $R^{26}$ are each deuterium (D). In some cases, s is 1. In certain instances, $R^{27}$ and $R^{26}$ are selected from D and F. In certain instances, $R^{27}$ and $R^{28}$ are each C(1-6)alkyl, such as methyl. In certain instances, $R^{27}$ and $R^{28}$ are each halogen, such as fluoro. In certain instances, $R^{27}$ and $R^{28}$ are each H. In certain instances, $R^{27}$ and $R^{28}$ are each deuterium (D). In some cases, p is 1.

In some embodiments of formula (B1.1a), the compound is of the formula:

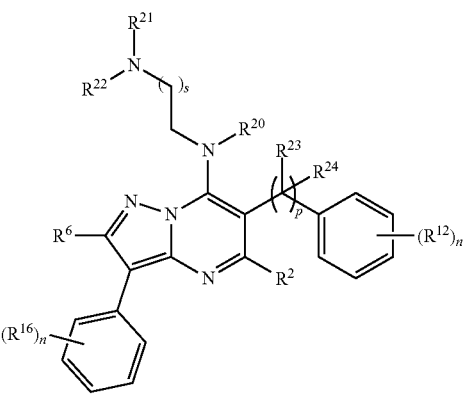

wherein:

each $R^{12}$ and $R^{16}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

s is 0-5 (e.g., s is 1-5 or 1-4, such as 1, 2 or 3) and p is 0-3 (e.g., 0, 1 or 2); each n is independently 0-5;

$R^{21}$ and $R^{22}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or $R^{21}$ and $R^{22}$ are cyclically linked and together with the N atom through which they are connected provide a 5 or 6-membered heterocycle that is optionally further substituted; and $R^{23}$ and $R^{24}$ are independently selected from H, alkyl and substituted alkyl or $R^{23}$ and $R^{24}$ are cyclically linked to provide a cycloalkyl or substituted cycloalkyl ring.

In certain instances, $R^2$, $R^6$ and $R^{20}$-$R^{24}$ are independently selected from H, C1-6alkyl and substituted C1-6alkyl. In some cases, $R^{20}$, $R^{23}$ and $R^{24}$ are each H. In certain instances, is 1. Each $R^{12}$ and $R^{16}$ can be independently selected from H, C1-6alkyl, substituted C1-6alkyl, C1-6alkoxy, substituted C1-6alkoxy, heterocycle, halogen, nitro, cyano and hydroxy.

In some embodiments of the formula above, s is 1 and p is 1. In some cases, the compound is of the formula:

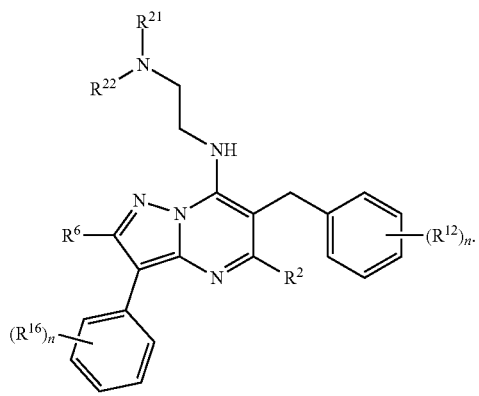

In certain cases, $R^2$, $R^6$, $R^{21}$ and $R^{22}$ are independently selected from H, C1-6alkyl and substituted C1-6alkyl.

In some embodiments of formulae (B1.1a), the compound has the following structure:

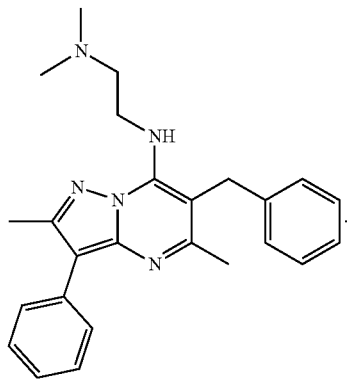 [SMILES: Cc1nc2c(-c3ccccc3)c(C)nn2c(NCCN(C)C)c1Cc1ccccc1]

Aspects of the present disclosure include RAS modulating compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds, prodrugs, stereoisomers or salts thereof are provided in the form of a solvate (e.g., a hydrate). The term "solvates" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include a RAS modulating compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the compound, as well as by the method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo (ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount enough to produce the desired effect in association with a pharmaceutically acceptable diluent, carrier or vehicle. The specifications for the novel unit dosage forms of the present disclosure depend on the compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be enough to affect a prophylactic or therapeutic response in the animal over a reasonable time frame, e.g., as described in greater detail herein. Dosage will depend on a variety of factors including the strength of the compound employed, the condition of the animal, and the body weight of the animal, as well as the severity of the illness and the stage of the disease. The size of the dose will also be determined by the existence, nature, and extent of any adverse side-effects that might accompany the administration of a compound.

Methods of Inhibiting Mutant RAS

The RAS modulating compounds of the present disclosure find use in modulating the activity of a target RAS in a sample. The target RAS can be a mutant RAS. Aspects of the subject methods include contacting the sample with an effective amount of a RAS modulating compound (e.g., as described herein). In some cases, an effective amount of a RAS modulating compound is an amount sufficient to inhibit the activity of the target RAS in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

In some cases, the target RAS is a mutant kRAS, a mutant nRAS or a mutant hRAS. The mutant RAS may be one that is responsible for a RAS-induced promotion of cell growth or proliferation in the sample. The subject methods can provide for modulation of the interaction of an activated GTP-bound RAS of interest with a RAF family protein. The subject methods can provide for partial or full blockage of the Ras-Raf-MEK-ERK pathway (MAPK pathway) to result in modulation of cell proliferation in a sample. In certain instances, the sample is a cellular sample and the cells are cancer cells of interest (e.g., as described herein). The sample can be in vitro or in vivo. In some instances, the subject methods result in inhibition or decrease of RAS-induced proliferation by 10% or more, such as 20% or more, 30% or more, 40% or more, 50% or more, 60% or more, 70% or more, 80% or more, 90% or more, or even more, relative to a control, e.g., cells not contacted with the compound of interest.

Aspects of the subject methods include evaluating the activity of the target RAS in the sample. As used herein, the terms "evaluating", "determining," "measuring," and "assessing," and "assaying" are used interchangeably and include both quantitative and qualitative determinations. Evaluating the activity of the target RAS can be performed before and/or after the sample is contacted with the subject compound and can be achieved using any convenient methods, including both direct methods (e.g., assays of GTPase activity or inhibition assays of direct binding of the target RAS) and indirect methods (e.g., measuring downstream signals produced by the Ras-Raf-MEK-ERK pathway or measuring cellular proliferation). Exemplary methods for evaluating the activity of the target RAS are described herein, for example, the cytotoxicity assay, the phosphorylated ERK bioassay, the cell morphology assay and the Fly assay of the Examples section.

Methods of Treatment

The RAS modulating compounds of the present disclosure find use in treatment of a condition or disease in a subject in which the activity of a mutant RAS GTPase is implicated (e.g., as described herein). Aspects of the method include administering to a subject in need thereof a therapeutically effective amount of a RAS modulating compound to treat the subject. By "a therapeutically effective amount" is meant the concentration of a compound that is enough to elicit the desired biological effect (e.g., treatment of the condition or disease). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms. In the context of cancer, the term "treating" includes any or all reducing of the growth of a solid tumor, inhibiting replication of cancer cells, reducing overall tumor burden, and ameliorating one or more symptoms associated with a cancer.

The subject to be treated can be one that needs therapy, where the host to be treated is one amenable to treatment using the RAS modulating compound. In some embodiments, the subject is one that has kRAS-driven cancer. In certain embodiments, the subject has a tumor with cells containing a kRAS G12V mutation. In some embodiments, the subject is one that has a hRAS-driven tumor. In some embodiments, the subject is one that has a nRAS-driven tumor. In another aspect, the subject is a child with one of many genetic conditions termed RASopathies, as described by Niemeyer CM (RAS diseases in children. Haematoiogica. 2014; 99:1653-62).

In some cases, the subject methods of treatment include a step of determining or diagnosing whether the subject has a disease associated with a mutant RAS GTPase. The determining step can be performed using any convenient methods. In some cases, the determining step includes obtaining a biological sample from the subject and assaying the sample for the presence of a mutant RAS. The sample can be a cellular sample. In some cases, the sample is a biopsy (e.g., a tumor biopsy). The determining step can include identification of cancer cells including a kRAS mutation. The determining step can include identification of cancer cells including a hRAS mutation. The determining step can include identification of cancer cells including a nRAS mutation. In certain cases, the subject has a MYH associated polyposis, and the determining step includes identifying cells that include a mutant hRAS or nRAS.

Accordingly, a variety of subjects may be amenable to treatment using the RAS modulating compounds and pharmaceutical compositions disclosed herein. As used herein, the terms "subject" and "host" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of RAS modulating compound administered can be determined using any convenient methods to be an amount enough to produce the desired effect in association with a pharmaceutically acceptable diluent, carrier or vehicle. The specifications for the unit dosage forms of the present disclosure will depend on the compound employed and the effect to be achieved, and the pharmacodynamics associated with each compound in the host.

In some embodiments, an effective amount of RAS modulating compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a RAS modulating compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the RAS modulating compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a target RAS. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of a mutant RAS or for the presence of cells that are associated with the disease or condition of interest (e.g., as described herein). The sample can be a cellular sample. In some cases, the sample is a biopsy. The assessment step(s) of the subject method can be performed at one or more times before, during and/or after administration of the subject compounds, using any convenient methods. In certain cases, the assessment step includes identification of cancer cells including a kRAS mutation. The determining step can include identification of cancer cells including a hRAS mutation. In certain instances, assessing the subject include diagnosing whether the subject has a MYH associated polyposis. In certain cases, assessing the subject includes identifying cells that include a mutant hRAS or nRAS.

Combination Therapy

Aspects of the present disclosure further include combination therapies. In certain embodiments, the subject method includes administering a therapeutically effective amount of one or more additional active agents. By combination therapy is meant that a RAS modulating compound (e.g., as described herein) can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or subsequent to administration of another therapeutic agent.

The subject compounds can be administered in combination with other therapeutic agents in a variety of therapeutic applications. Therapeutic applications of interest for combination therapy include those applications in which activity of a mutant RAS is the cause or a compounding factor in disease progression. As such, the subject compounds find use in combination therapies in which the inhibition of a target RAS in the subject is desired. Examples of disease conditions which may be treated by a combination therapy including a subject compound include, but are not limited to, cancer and MYH associated polyposis.

The subject RAS modulating compounds can be used jointly with any agent useful in the treatment of a neoplastic condition, such as anti-cancer agents and anti-tumor agents. One class of anti-cancer agents of interest includes chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation.

Agents of interest which can be used in jointly with the subject RAS modulating compounds include, but are not limited to, Cancer chemotherapeutic agents, Agents that act to reduce cellular proliferation, Antimetabolite agents, Microtubule affecting agents, Hormone modulators and steroids, natural products and Biological response modifiers, e.g., as described in greater detail below.

Cancer chemotherapeutic agents include non-peptidic (i.e., non-proteinaceous) compounds that reduce proliferation of cancer cells and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1), and benzodiazepines and active analogs and derivatives thereof (e.g., pyrrolobenzodiazepine (PBD).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and progestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine;

epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl) propoxy) quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*). Paclitaxel should be understood to refer to not only the common chemically available form of paclitaxel, but analogs and derivatives (e.g., Taxotere□ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfonamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Utility

The RAS modulating compounds, e.g., as described herein, find use in a variety of applications. Applications of interest include but are not limited to: therapeutic applications and research applications. RAS modulating compounds of the present disclosure and pharmaceutical compositions including the same find use in a variety of therapeutic applications. Therapeutic applications of interest include those applications in which a target RAS GTPase activity is the cause or a compounding factor in disease progression. As such, the subject compounds find use in the treatment of a variety of different conditions in which the modulation of a target RAS in the host is desired. Examples of disease conditions which may be treated with compounds of the invention include, but are not limited to: cancer, MYH associated polyposis and RASopathies.

The subject compounds and compositions find use in treatment of a variety of cancers, including but not limited to, pancreatic cancer, colon cancer, endometrial cancer, lung adenocarcinoma, skin cancer, acute myeloid leukemia (AML) and multiple myeloma. In certain instances, the target RAS is a mutated kRAS implicated in pancreatic cancers, colon cancers, endometrial cancers, lung adenocarcinomas, eg, non-small cell lung carcinoma (NSCLC), skin cancers, acute myeloid leukemia (AML) liquid tumors or a multiple myeloma cancer.

The subject compounds and compositions find use in treatment of MYH associated polyposis, a hereditary condition characterized by a tendency to develop multiple adenomatous colon polyps with a concomitant increased risk of colorectal cancer. In some instances, patients who may be treated according to the subject methods also possess a mutated kRAS gene/protein. The subject compounds and compositions also find use in treatment of a genetic condition termed RASopathy, as described by Niemeyer CM (RAS diseases in children, Haematologica. 2014; 99:1653-62). In such applications, the patient can be one that has a kRAS, hRAS or nRAS mutation, such as a G12V mutation.

The subject compounds find use in a variety of research applications including the identification and testing of candidate RAS modulating compounds (e.g., for pharmaceutical development) and performing research on disease conditions of interest in which the activity of a target RAS GTPase is implicated. Research applications of interest can involve use of the subject compounds in a variety of in vitro assays including high throughput screening assays, potency assays, and competitive inhibition assays where the subject compounds can be useful as a control compound or as a tool in the investigation the pathology of cells of interest.

Systems and Kits

Also provided are kits that include RAS modulating compounds (e.g., as described herein). Systems of the present disclosure include collections of active agents brought together, e.g., by a health care practitioner, for administration to a subject, such as a patient. Such systems may include a RAS modulating compound and one or more additional active agents (e.g., as described herein). Kits that include RAS modulating compounds which are provided that may include one or more dosages of a RAS modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al, eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1

Introduction

The Tosk approach uses *Drosophila melanogaster* flies as media for initial screening for RAS modulating compounds. Tosk has created a fruit fly with human kRAS G12V expressed in its wing. The mutant kRAS expressed in the fly wing appears functional, even though it operates in the presence of the other physiological systems present in the fly. The fly phenotype in the mutant fly is a crimped wing which can be reversed to a great extent if the fly is fed food enriched with an effective kRAS inhibitor. The fly kRAS suppressor screen can provide a more predictive model compared to conventional discovery methods because the kRAS is in its natural (i.e., not artificial/isolated/manipulated) environment anchored to the plasma membrane, positioned correctly, and surrounded by appropriate neighboring chemicals. Several reports have emphasized the importance of kRAS positioning and environment to realize protein activity.

The fly screen can provide hit compounds that otherwise might not be discovered. Also, compounds active in the fly must also be bioavailable when administered in the food, and toxic compounds will most likely prevent the development of the flies, and, therefore, will not register as hits. Finally, "off-target" hits in the fly can be more easily identified as such when evaluated in the mammalian test systems at Tosk, e.g., the test article works in fly but shows no activity in human cancer cell lines. The kRAS fly screen is used to identify exemplary compounds based on chemical scaffolds capable of optimization into lead candidate compounds.

The present disclosure describes discovery of a class of kRAS inhibitors using a fly screen to test a commercially available chemical library. One of the exemplary inhibitors identified in this screen as the result of its ability to reverse the crinkled wing phenotype from expression of human G12V kRAS in the wing of the animal is Structure 1. This disclosure provides a class of compounds related to Structure 1 having anti-kRAS activity.

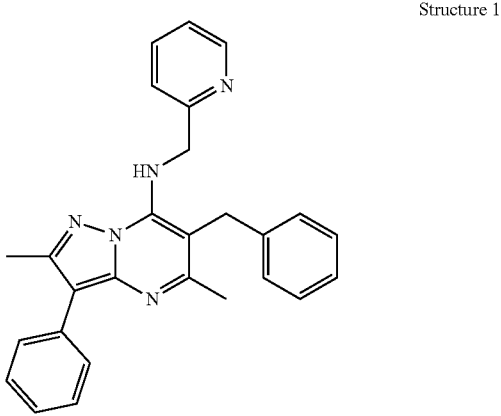 [SMILES: Cc1nc2c(-c3ccccc3)c(C)nn2c(NCc2ccccn2)c1Cc1ccccc1]

Structure 1

Effect of Structure 1 on Viability of Cancer Cells Whose Growth is Driven by Mutated kRAS Protein Mutations in the kRAS gene produce proteins, eg, kRAS G12V, G12D, G12C, G13D, Q61H, etc. that promote cell growth. In this regard, inappropriate and undifferentiated cell growth is a cardinal feature of cancer.

Structure 1 was identified as described below using a drug screen that utilizes transgenic fruit flies. The compound reverses a distorted wing phenotype induced by expression of mutant human kRAS (G12V) in the wings of the animals. The excess kRAS present in the wing because of the transgenic expression, is believed to inappropriately accelerate growth of cells in the wing in an unsynchronized fashion resulting in a crinkled, non-functional wing phenotype.

The screening effort established that Structure 1 inhibited the human kRAS in the wing and restored normal, synchronized wing growth. Additional studies in alternate test systems were performed to support the conclusion from the fly screen.

Structure 1 was assayed for inhibition of cell proliferation and killing cancer cells. Cytotoxicity assays were conducted according to the following general procedure. SW620, SW1990, etc, were all maintained in Leibowitz L15 media supplemented with 10% fetal bovine serum and 1% Pen-Strep and grown in a 37° C. incubator without supplemental $CO_2$. Cells were plated into 96 well flat bottom plates (2 million/plate, ~20,000/well, 200 µL media/well). The cells were allowed to settle and adhere to plate bottom overnight.

Compounds were diluted in media from a 10 mM stock solution starting at 50 µM, using 2-fold dilutions, in a column in a 96-well plate. Media was removed from the plate containing cells and replaced with media containing diluted compounds. Plates were incubated 72 hours at 37° C. with no supplementary $CO_2$. Plates were allowed to come to room temperature. and 100 µL CellTiter-Glo 2.0 reagent (Promega, G9240) was added at room temperature. Plates were shaken for 2 minutes, then allowed to stand for 15 minutes. Luminescence was read with a FLx800 (BioTek Instruments).

A dose response curve for the cytotoxicity of Structure 1 against SW620 human cancer cells is shown in FIG. 1. SW620 cancer cells are derived from an adenocarcinoma colon cancer sample from a 51-year-old male Caucasian. SW620 cells are driven by a G12V kRAS mutation and are tumorigenic in nude mice. The $IC_{50}$ for Structure 1 in the SW620 cells was determined to be 3.9 µM.

Figure 2:
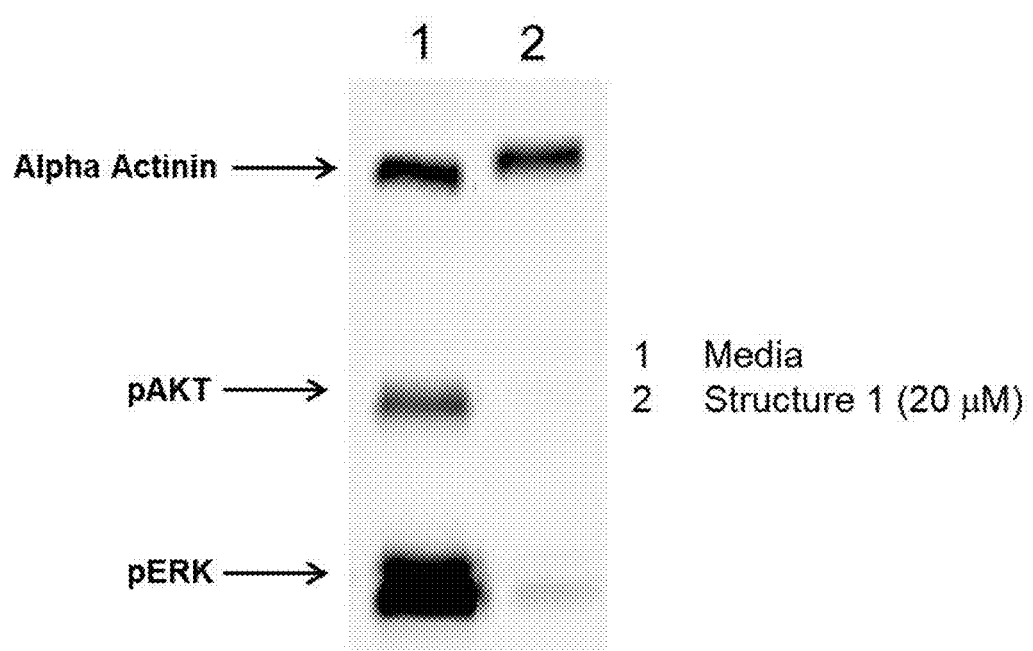
FIG. 2 shows a gel chromatogram illustrating the effect of Structure 1 on phosphorylated ERK (extracellular signal regulated kinases) and phosphorylated AKT (protein kinase B), two downstream effectors of kRAS. Structure 1 decreased both phosphorylated AKT and phosphorylated ERK. Structure 1 had no effect on AKT or ERK (data not shown).

The exemplary compound was also tested at 3 µM for protein kinase inhibition against the following protein kinases: AKT1, AKT2, AKT3, EGF-R, EGF-R (L858R mutation), FRAP1, GSK3B, MAPK1 (ERK2), MAPK3 (ERK1), BRAF, BRAF V599E, MAP2K1 (MEK1), MAP2K2 (MEK2), PDK1, RAF1, PI3K C2A, PI3K C2B, PI3K C3, PI3K 3A, PI3K CB, PI3K CD, and PI3K CG. No kinase inhibitory activity was observed in any of the assays eliminating the possibility of one common off-target for possible inhibitors of the kRAS protein. FIG. 2 shows the Fly Effect of Structure 1 on Phosphorylated ERK and Phosphorylated AKT, two downstream effectors of kRAS. The main downstream targets for kRAS are ERK (Samatar et al., Targeting RAS-ERK signaling in cancer: promises and challenges. Nat Rev Drug Discov. 2014; 13:928-42 and Martini et al., Ann Med. 2014; 46:372-83). kRAS activates ERK and AKT leading to phosphorylated ERK and phosphorylated AKT. A compound that suppresses kRAS activity is expected to lower phosphorylated ERK and phosphorylated AKT.

A method used to measure ERK and AKT is based on Welsch et al, Cell 168: 878-889 February 2017. SW1990 cells, growth driven by a G12D kRAS mutation and derived from human, pancreatic cancer cells, are plated in a 6-well plate at $1.5 \times 10^6$ cells per plate and grown overnight at 37° C. Media is replaced with serum-free media and the plate incubated an additional 24 hours. Media is replaced with media with or without compound and incubated for an additional 24 hours. EGF is added at a concentration of 10 ng/mL. After 15 minutes, cells are washed with ice cold PBS and lysed with RIPA buffer.

The lysate is processed by electrophoresis using a Mini-PROTEAN® gel mounted in a Mini-PROTEAN® Tetra Cell (cassette). Both the gel and the holding assembly (cassette) are purchased from BIORAD. The gel in the assembly is placed, electrode up, in the buffer tanks. The Tris/glycine/SDS buffer is added to both the inner buffer chamber (200 mL) and the outer buffer chamber (800 mL). The sample (approximately 1 µg) is loaded onto the gel and electrophoresis performed at 100 volts and 20 ma for ten minutes followed by 200 volts and 40 ma for 20 minutes. The electrophoresis is stopped when the dye from the front reached the reference line imprinted on the bottom of the cassette.

The gel is removed from the electrophoresis assembly and equilibrated in Towbin transfer buffer. The gel is then transferred, along with the supported nitrocellulose membrane into a BioRad Mini Trans Blot cassette. The tank is filled with Towbin buffer and a stirring bar added. A 100 ma current is applied for approximately one hour.

The membrane is placed into TTBS buffer containing SuperBlock T20 (Thermo Scientific) and incubated for 1 hour at room temperature. The membrane is then incubated with rabbit anti-pERK, rabbit anti-pAKT and rabbit anti-alpha-actinin antibodies in SuperBlock for approximately one hour. The anti pERK detected both pERK 1 and 2 (T202/Y204). This is followed by incubation with secondary (detection) antibodies, HRP conjugated Goat anti-Rabbit in SuperBlock for one hour and the detection is by chemiluminescence reaction Pierce ECL Western Blotting Substrate. All antibodies are obtained from Cell Signaling, Inc.

The results of the assay with exemplary Structure 1 are provided in FIG. 2. Structure 1 suppressed phosphorylated ERK and phosphorylated AKT without affecting non-phosphorylated ERK or non-phosphorylated AKT.

Example 2

Preparation of the G12V Mutant Fly used in Screening for RAS Modulating Compounds A scheme for preparation of G12V transgenic flies is as follows:
1. Make Gene. Human G12V kRAS gene, flanked by Bgl II and Xho I sites synthesized by GeneCopeia (Rockville, Md.). Sequence encodes a 188 amino acid gene for kRAS 4B protein in which valine has been substituted for glycine at position 12.
2. Make Vector. The G12V kRAS gene was then inserted into the pUAST vector for the purpose of producing *Drosophila melanogaster* with human kRAS. For insertion of human kRAS into the pUAST vector, pUAST was digested with Bgl II and Xho I, and the Bgl II Xho I fragment from the G12V kRAS GeneCopeia shuttle vector inserted.
3. Make Fly. The pUAST-G12V kRAS plasmid was sent to BestGene, Inc., for transformation into the fly genome. Personnel at BestGene recovered transgenic adult flies with kRAS inserted on the first, second and third chromosomes. The *Drosophila* background was w118. The transgenic lines were delivered to Tosk as balanced stocks.

Production of the Transgenic Fly Expressing G12V Used in Screening for RAS Modulating Compounds A scheme for production of the transgenic fly is as follows:
1. Cross. Females of the GAL4 expressing fly strain 8860 (w[1118] P{w[+mW.hs]=GawB}Bx[MS1096] from the *Drosophila* Stock Center, Bloomington, Ind., are crossed with the male G12V kRAS flies possessing a UAS enhancer element.
2. Fly with Crinkled Wing Phenotype. The wings of flies with G12V kRAS expressed in their wings showed a distinct crimped/crinkled phenotype Fly Screen Used in Screening for RAS Modulating Compounds A scheme for the fly screen is outlined below.
1. Production of Fly Food/Test Article Mix. A Biomek 2000 robotic arm is used to pipet 40 µL of a 10 mM DMSO solution of Test Article into a 35 mL polypropylene *Drosophila* fly vial (VWR 89092-728) containing 10 mL ETOH. A half teaspoon blue fly food (4-24, Carolina Biological Supply), is added and the tubes are vortexed and placed into a HT-4X GeneVac to remove the DMSO and ETOH. The tube is vortexed, 4 ml water added, and vortexed again. Control samples are tubes with fly food prepared with just 40

μL DMSO, no Test Article, or 40 μL of a DMSO solution containing 50 μM of the trametanib positive control.

2. Screen. Several hundred male G12V kRAS flies and several hundred GAL4 females are placed in a custom Plexiglas population cage (12"×12"×8") made fly condo containing grape agar and yeast paste prepared using a published protocol. Embryos from the container are washed off the grape agar onto a sieve and re-suspended in an aqueous sucrose/salt/triton solution. An aliquot of this solution is analyzed using a dissecting microscope to determine the embryo concentration. The appropriate solution to deliver 150 embryos is then added to the fly food/Test article vials. The vial is capped with a cellulose fly bottle plug. Using the recipe provided above, the final concentration of Test Article in the mixture is ~100 μM. The vials are incubated at 23° C. in a temperature-controlled room for 12 days.

3. Analysis. After 12 days, all flies in a vial are observed under a microscope following $CO_2$ anesthesia for the number of phenotype reversals compared to the total number of viable flies. Cell culture testing is typically performed for any Test Article showing evidence of >25% phenotype reversal. The trametinib positive control provides reversal of the crimped/crinkled phenotype for 50-75% of the flies.

Figure 3:
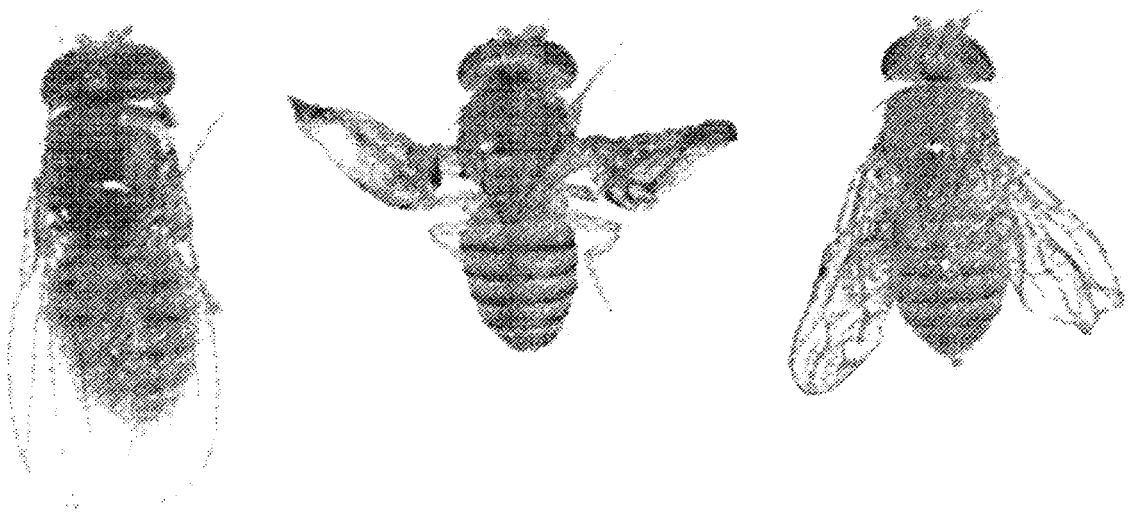
FIG. 3 shows images of normal flies, untreated G12V flies, and flies expressing G12V in their wing which are treated with trametinib, a MEK inhibitor used as positive control in the assay.

FIG. 3 shows pictures of a control fly, a fly with G12V kRAS expressed in the wings and processed through the screen, and a fly with G12V kRAS expressed in the wings, treated with trametinib and processed through the screen. Trametinib is a positive control in the fly screen assay.

Example 3

Identification of Structure 1

A library of over 16,000 distinct chemicals was purchased from ChemDiv, San Diego, Calif. All the compounds were evaluated in the fly screen described above for the ability to reverse the crinkled wing phenotype. Of the 16,000 compounds only three reliably reversed the phenotype. One of the three compounds was Structure 1. Data for Structure 1 is provided in Table 4.

Table 4 provides information on two separate fly screening experiments. In the first experiment, Structure 1 compound provided over 2.5-fold more flies with the phenotype reversals (75%) than the positive control, trametinib (29%). In the second experiment, Structure provided approximately the same percent reversal as the trametinib, 58% versus 63 and 64%, respectively.

TABLE 4

Fly Screening Results for Structure 1 compound.

| Concentration (μM) | Experiment | Flies with Reversed Phenotype (%) |
|---|---|---|
| 0 (DMSO) | 1 | 1.9 |
| 0 (DMSO) | 1 | 1.4 |
| 0.5 (Trametinib) | 1 | 29 |
| 0.5 (Trametinib) | 1 | 29 |
| 20 (Structure 1) | 1 | 75 |
| 0 (DMSO) | 2 | 0 |
| 0 (DMSO) | 2 | 3.3 |
| 0.5 (Trametinib) | 2 | 63 |
| 0.5 (Trametinib) | 2 | 64 |
| 20 (Structure 1) | 2 | 58 |

Synthesis

Compounds of interest can be prepared by adapting any convenient synthetic methods and synthons. For example, compounds based on a pyrrolopyrimidine scaffold may be prepared by adapting methods reviewed by Amarnath and Madhav, "A Survey of Methods for the Preparation of Pyrrolopyrimidines", Synthesis 1974; 1974(12): 837-859.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A RAS modulating compound of formula (B1.1):

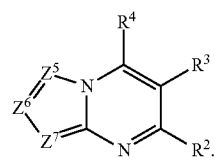

(B1.1)

wherein:

$Z^5$ is N, $CR^5$ or $NR^5$;

$Z^6$ is N, $CR^6$ or $NR^6$; and $Z^7$ is N, $CR^7$ or $NR^7$;

$R^2$-$R^7$ are independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino, and/or wherein any two ortho $R^1$-$R^7$ groups can be cyclically linked to provide an (mho-fused 5-membered carbocyclic or heterocyclic ring optionally further substituted;

at least one of $R^2$, $R^6$ and $R^7$ is selected from aryl, substituted aryl, heteroaryl and substituted heteroaryl; and wherein when $R^7$ is selected from aryl, substituted aryl, heteroaryl and substituted heteroaryl, $R^7$ is bound to n R groups, wherein each R in the n R groups is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino, and n is 0-5;

or a salt thereof, or a solvate, enantiomer, hydrate or prodrug form thereof.

2. The compound according to claim 1, wherein the compound is of one of the formulae:

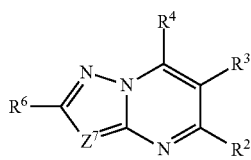

(B1.1a)

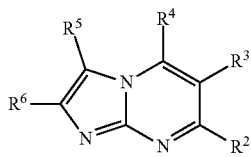

(B1.1b)

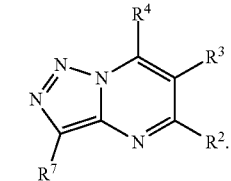

(B1.1c)

3. The compound according to claim 2, wherein the compound is of formula (B1.1a) wherein $Z^7$ is N.

4. The compound according to claim 2, wherein the compound is of formula (B1.1a) wherein $Z^7$ is $CR^7$.

5. The compound according to claim 1, wherein:

$R^2$-$R^7$ are independently selected from H, alkyl, substituted alkyl, aryl, substituted aryl, heteroaryl, substituted heteroaryl, heterocycle, substituted heterocycle, alkoxy, substituted alkoxy, alkylamino and substituted alkylamino.

6. The compound according to claim 1, wherein $R^7$ is selected from aryl, substituted aryl, heteroaryl and substituted heteroaryl.

7. The compound according to claim 1, wherein $R^6$ is selected from aryl, substituted aryl, heteroaryl and substituted heteroaryl.

8. The compound according to claim 7, wherein $R^2$ is selected from aryl, substituted aryl, heteroaryl and substituted heteroaryl.

9. The compound according to claim 1, wherein:

$R^4$ is —$NR^{25a}R^{25b}$; and $R^{25a}$ and $R^{25b}$ are independently selected from H, alkyl, substituted alkyl, aryl, substituted aryl, heteroaryl, substituted heteroaryl, alkylsulfonyl, substituted alkylsulfonyl, alkanoyl and substituted alkanoyl, or $R^{25a}$ and $R^{25b}$ are cyclically linked and together with the N atom through which they are connected provide a 5 or 6-membered heterocycle that is optionally further substituted.

10. The compound according to claim 4, wherein the compound is of the formula:

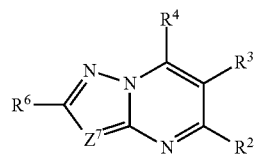

(B1.1a)

wherein:

$Z^7$ is $CR^7$;

$R^2$ is selected from H, alkyl, substituted alkyl;

$R^3$ is selected from aryl-alkyl, substituted aryl-alkyl, heteroaryl-alkyl, substituted heteroaryl-alkyl, aryl, substituted aryl, heteroaryl and substituted heteroaryl;

$R^4$ is —$NR^{25a}R^{25b}$;

$R^6$ is selected from H, alkyl and substituted alkyl;

$R^7$ is selected from aryl, substituted aryl, heteroaryl and substituted heteroaryl; and $R^{25a}$ and $R^{25b}$ are independently selected from alkyl, substituted alkyl, aryl, substituted aryl, heteroaryl, substituted heteroaryl, alkylsulfonyl, substituted alkylsulfonyl, alkanoyl and substituted alkanoyl, or $R^{25a}$ and $R^{25b}$ are cyclically linked and together with the N atom through which they are connected provide a 5 or 6-membered heterocycle that is optionally further substituted.

11. The compound according to claim 10, wherein the compound is of the structure:

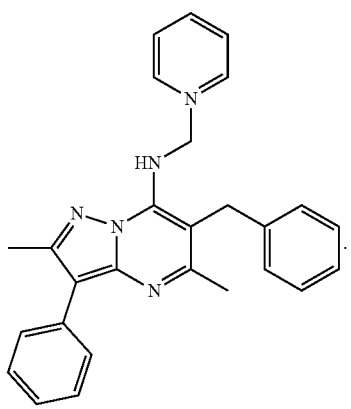

12. The compound according to claim 10, wherein the compound is of the formula:

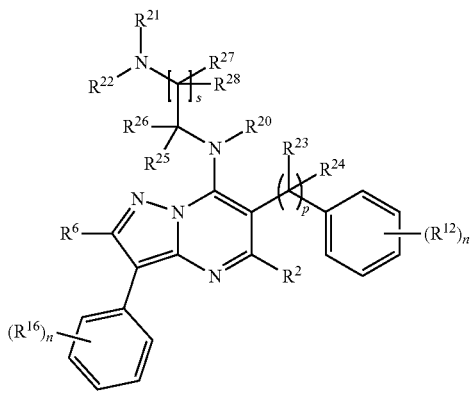

wherein:
  each $R^{12}$ and $R^{16}$ is independently selected from alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
  each n is independently 0-5;
  s is 0-5 (e.g., s is 1-5, such as 1, 2 or 3);
  $R^{20}$ to $R^{22}$ are independently selected from alkyl, substituted alkyl, aryl, substituted aryl, heteroaryl, substituted heteroaryl, alkylsulfonyl, substituted alkylsulfonyl, alkanoyl and substituted alkanoyl, or $R^{21}$ and $R^{22}$ are cyclically linked and together with the N atom through which they are connected provide a 5 or 6-membered heterocycle that is optionally further substituted;
  $R^{23}$ and $R^{24}$ are independently selected from H, alkyl and substituted alkyl or $R^{23}$ and $R^{24}$ are cyclically linked to provide a cycloalkyl or substituted cycloalkyl ring; and
  $R^{25}$ to $R^{28}$ are each independently selected from H, D, halogen (e.g., alkyl (e.g., methyl) and substituted alkyl.

13. The compound according to claim 12, wherein the compound has the following structure:

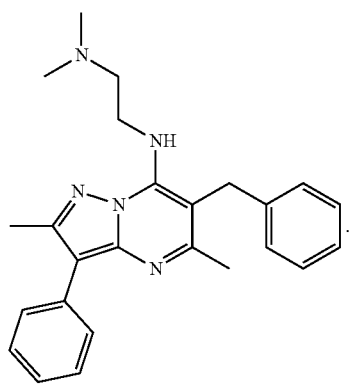 [SMILES: Cc1nc2c(-c3ccccc3)c(C)nn2c(NCCN(C)C)c1Cc1ccccc1]

14. The compound according to claim 1, wherein the compound is of one of the formulae:

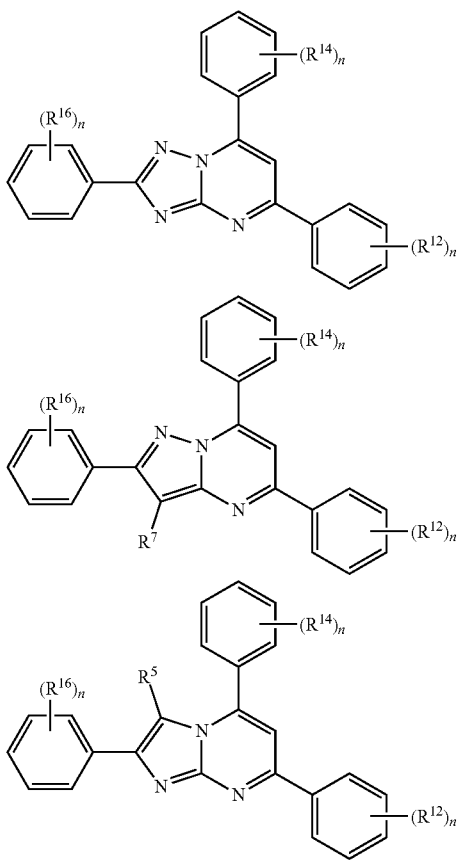

wherein:
  each $R^{12}$, $R^{14}$ and $R^{16}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
  each n is independently 0-5; and
  $R^5$ and $R^7$ are independently H, alkyl or substituted alkyl.

15. The compound according to claim 6, wherein the compound is of one of the formulae:

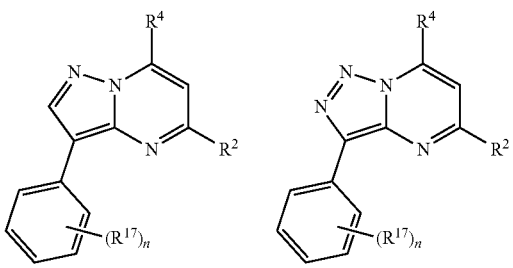

wherein:
each $R^{17}$ is independently selected from H, alkyl, substituted alkyl, aryl, substituted aryl, heteroaryl, substituted heteroaryl, heterocycle, substituted heterocycle, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino; and n is 0-5.

16. The compound according to claim 15, wherein the compound has one of the following structures:

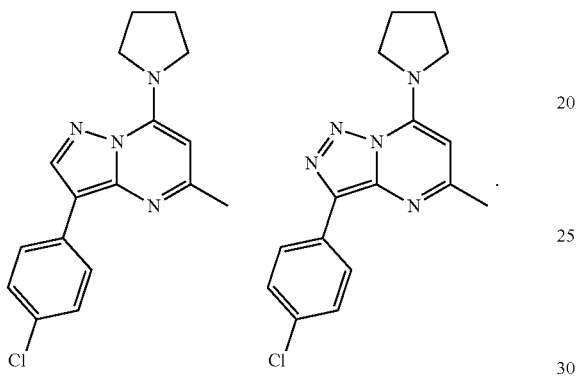

UNITED STATES PATENT AND TRADEMARK OFFICE
CERTIFICATE OF CORRECTION

PATENT NO. : 11,390,626 B2
APPLICATION NO. : 16/774381
DATED : July 19, 2022
INVENTOR(S) : William A. Garland et al.

Page 1 of 2

It is certified that error appears in the above-identified patent and that said Letters Patent is hereby corrected as shown below:

In the Specification

Please replace "Task" with -- Tosk -- (Column 2, Line 4).

Please replace "DURAS" with -- DIRAS -- (Column 5, Line 43).

Please replace "D1RAS2" with -- DIRAS2 -- (Column 15, Line 25).

Please replace " 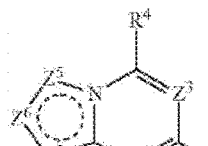 " with -- 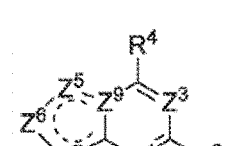 -- (Column 17, Lines 21-30).

Please replace "formula (81.1)" with -- formula (B1.1) -- (Column 18, Line 33).

Please replace "(81.1a)" with -- (B1.1a) -- (Column 22, Line 63).

Please replace "$R^{26}$" with -- $R^{28}$ -- (Column 25, Line 51).

Please replace "Haematoiogica" with -- Haematologica -- (Column 33, Lines 14-15).

Please replace "progestins" with -- pregestins -- (Column 36, Line 51).

Please replace "sulfonamide" with -- sulfenamide -- (Column 37, Line 37).

Please replace "w118" with -- w1118 -- (Column 42, Line 37).

Signed and Sealed this
Thirteenth Day of September, 2022

Katherine Kelly Vidal
*Director of the United States Patent and Trademark Office*

CERTIFICATE OF CORRECTION (continued)
U.S. Pat. No. 11,390,626 B2

In the Claims

Please replace "(mho-fused" with -- ortho-fused -- (Column 45, Line 3).

Please replace "from alkyl" with -- from H, alkyl -- (Column 46, Line 39).

Please replace "from alkyl" with -- from H, alkyl -- (Column 47, Line 22).

Please replace "from alkyl" with -- from H, alkyl -- (Column 47, Line 35).

Please replace "(e.g., alkyl (e.g., methyl)" with -- (e.g., F), alkyl (e.g., methyl) -- (Column 47, Line 47).